United States Patent
Plumb et al.

(10) Patent No.: US 7,418,352 B2
(45) Date of Patent: Aug. 26, 2008

(54) METHOD OF USING DATA BINNING IN THE ANALYSIS OF CHROMATOGRAPHY/SPECTROMETRY DATA

(75) Inventors: Robert Stephen Plumb, Milford, MA (US); Chris Lee Stumpf, Uxbridge, MA (US); Marc V. Gorenstein, Needham, MA (US)

(73) Assignee: Waters Investments Limited

( * ) Notice: Subject to any disclaimer, the term of this patent is extended or adjusted under 35 U.S.C. 154(b) by 0 days.

(21) Appl. No.: 11/480,254

(22) Filed: Jun. 30, 2006

(65) Prior Publication Data

US 2007/0083337 A1  Apr. 12, 2007

Related U.S. Application Data

(63) Continuation of application No. 10/989,533, filed on Nov. 16, 2004, now Pat. No. 7,072,773, which is a continuation of application No. PCT/US03/17190, filed on May 30, 2003.

(60) Provisional application No. 60/384,712, filed on May 31, 2002.

(51) Int. Cl.
   *G06F 19/00* (2006.01)
   *G06F 11/30* (2006.01)
   *H01J 49/00* (2006.01)

(52) U.S. Cl. ..................... 702/32; 702/182; 250/281; 250/282

(58) Field of Classification Search ............. 702/28, 702/32, 40, 179, 182, 190; 250/281, 182, 250/282; 386/46, 69
See application file for complete search history.

(56) References Cited

U.S. PATENT DOCUMENTS 5,175,430 A * 12/1992 Enke et al. ............... 250/282
6,182,016 B1 * 1/2001 Liang et al. ............... 702/22

\* cited by examiner

*Primary Examiner*—Bryan Bui
(74) *Attorney, Agent, or Firm*—Anthony J. Janiuk; Jamie H. Rose

(57) ABSTRACT

Disclosed herein is a method of analyzing three-dimensional data obtained from a chromatography/spectrometry process, in particular an LC/MS process using a two-dimensional multi-variant statistical analysis. The LC portion permits separation of analytes within a sample. The information obtained from such a procedure typically depends on retention time ($R_t$). As the analytes progress through the system, they enter the MS region of the LC/MS system. There they are ionized and a mass detector then detects these ionized species. The information procured from this procedure is generally reported as intensity for a corresponding m/z value. Therefore, an LC/MS system provides at least three pieces of information. Principle component analysis (PCA) is a robust method of multi-variant analysis of this type of data between different samples. However, typically, PCA analysis is performed using only two-dimensional data. Therefore, it is expected that at least one parameter of data obtained from a LC/MS operation is lost, however, the methods disclosed herein preserves all three mathematical dimensions.

12 Claims, 13 Drawing Sheets

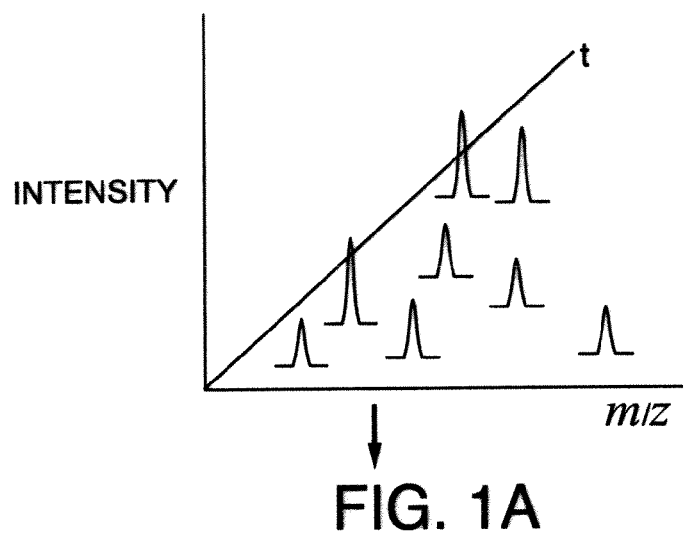
FIG. 1A
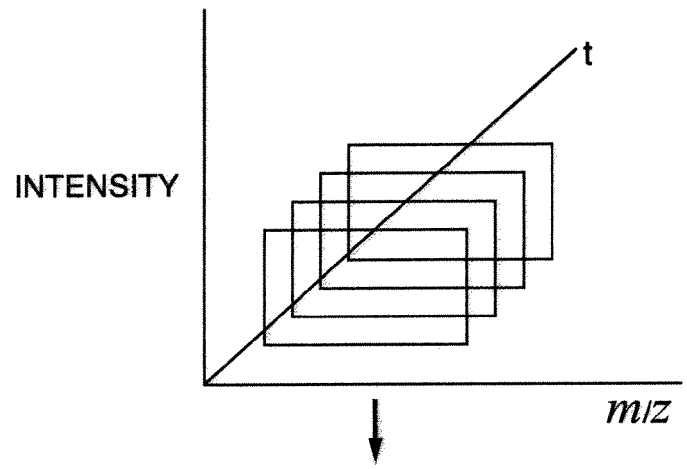
FIG. 1B
| m/z | 1 | 2 | 3 | 4 BIN |
|---|---|---|---|---|
| 100 | 20 | 30 | 50 | 0 |
| 120 | 50 | 0 | 100 | 10 |
| 140 | 30 | 10 | 0 | 115 |
| 160 | 100 | 15 | 20 | 60 |
| 180 | 10 | 80 | 120 | 85 |
| 200 | 45 | 30 | 130 | 20 |
| 220 | 20 | 35 | 45 | 10 |
↓
PCA
FIG. 1C

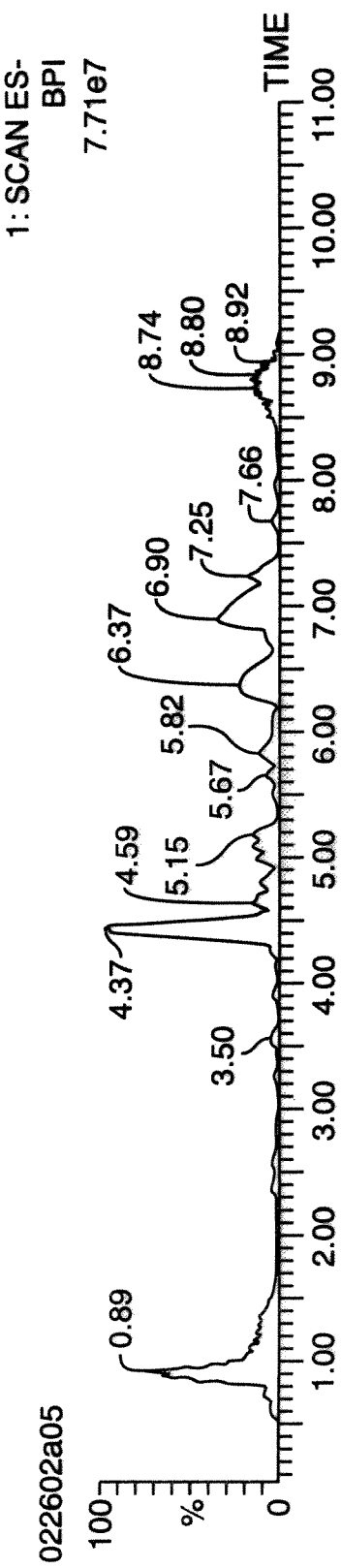
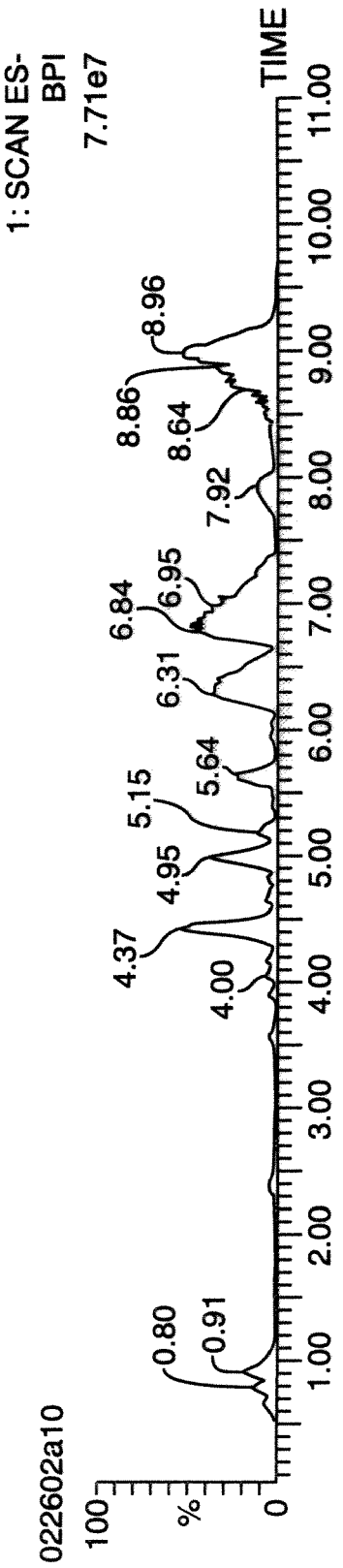
FIG. 2A
FIG. 2B

METHOD OF USING DATA BINNING IN THE ANALYSIS OF CHROMATOGRAPHY/SPECTROMETRY DATA

CROSS REFERENCE TO RELATED APPLICATIONS

This application is a continuation of U.S. patent application Ser. No. 10/989,533, filed on Nov. 16, 2004, which claims benefit of PCT Application No. PCT/US03/17190, which designated the U.S. and was filed on May 30,2003, which claims benefit of U.S. application No. 60/384,712, filed May 31, 2002. The contents of these applications are expressly incorporated herein by reference in their entirety.

FIELD OF THE INVENTION

The present invention relates to a method of analysis of multi-dimensional data by an analysis method applicable to fewer dimensions by the application of data binning to the data In particular, the present invention relates to a method for the analysis of chromatography/spectrometry data using data binning The invention has specific application to methods of doing liquid chromatography/mass spectrometry (LC/MS) data analysis employing data binning combined with principle component analysis.

BACKGROUND OF THE INVENTION

Metabonomics is a rapidly growing area of scientific research. It is a systems approach for studying in vivo metabolic profiles and can provide information on a particular disease, toxicity, and gene function. In metabonomics, the effect of a pharmaceutical candidate on a whole animal or organism is investigated by studying the changes in metabolism over a time course following compound administration. The analytical data generated in these studies is analyzed by multi-variant mathematical techniques such as Principle Component Analysis (hereinafter "PCA"). This mathematical technique is employed to highlight both subtle and gross differences in the samples being examined.

To date, the vast majority of work in this field has utilized proton-nuclear magnetic resonance (NMR) as the analytical method of choice. While being very effective, NMR has several disadvantages, namely, poor sensitivity, time consuming analysis, and the non-detection of some chemical classes, e.g., sulfates. A further draw back to NMR is that as all of the signals are contained in one spectrum it is easy for one large compound to mask subtle but important changes in a low concentration analyte. Further, the necessary removal of xenobiotic-related compounds from the NMR spectrum also removes signals from endogenous compounds of interest thus reducing the data set used for subsequent PCA analysis.

Chromatography, both gaseous and liquid, combined with spectrometric analysis such as ultraviolet spectroscopy, infrared spectroscopy, nuclear magnetic resonance or mass spectrometry, has evolved into a powerful technique. Electrospray mass spectrometry coupled with liquid chromatography (LC/MS) has become the technique of choice for bioanalysis, both quantitative and qualitative. The technique is robust, sensitive, and selective with sensitivities up to the pg/mL range readily achieved. The use of short columns and rapid gradients has also allowed LC/MS to achieve analytical cycle times in the region of one sample per minute with good chromatographic resolution and sensitivity. Thus the application of LC/MS to metabonomics is a logical step. While the mass spectrometer will give both high sensitivity quantitation and structural information, the chromatography step will address the issue of overlapping signals by separating out the analyte giving a time resolution The use of LC/MS is preferred over mass spectrometry infusion as the chromatography step reduces ion suppression by reducing the number of competing ions going into the mass spectrometer at any given time. Another advantage of LC/MS over NMR is observed in data analysis. When removing xenobiotic-related material only a small time slice at one or two specific masses will be removed from the data set. Therefore, the remaining LC/MS data is left unaltered and available for mathematical analysis, e.g., PCA.

Principle component analysis is a very effective mathematical device for analyzing the data obtained from MS. However, PCA is a two-dimensional technique whereas data obtained from LC/MS is three-dimensional. Curly, there exists a need to enable PCA to maintain the chromatographic separation information that is normally lost in conventional PCA analysis.

In general, there are many experimental conditions where the information about the results is contained in data that is characterized by multiple parameters. When the interpretive tools cannot handle these parameters, information is lost A methodology that improves the resolution of analysis of LC/MS data that is analyzed by the PCA process is applicable to other data sets.

SUMMARY OF THE INVENTION

This invention pertains to a method of analyzing multi-dimensional data using a tool that handles fewer dimensions. In a particular embodiment, this invention pertains to a method of analyzing the three-dimensional data obtained from a chromatography/spectrometry run, such as an LC/MS run using a two-dimensional multi-variant statistical analysis technique such as PCA. Typically, PCA analysis is performed using only two dimensional data. In the present invention, the analysis is performed using three-dimensional data.

Data obtained from a chromatography operation is characterize by a number of parameters. In particular, the chromatography separates the sample as a function of time. Retention time, the length of time a component of the sample is retained on the solid phase is particularly informative. Different components of the sample elute from the solid phase at different times depending on the conditions. This time dependant characteristic is useful in differentiating particular components of the sample.

Further parameters may be specific to the detection method used after the chromatography separation. For instance, in fluorescence detection the parameters of interest are wavelength and intensity of light, while in ultraviolet detection, a parameter of interest is the amount of absorbed light. In many cases, the greater the number of parameters an analysis method can handle, the more discriminating the result. When one parameter must be ignored entirely, the opportunity to discriminate between data points that differ only by that parameter is lost.

Data obtained from an LC/MS operation consists of three parameters. The first of these parameters is specific to the LC portion of the system Liquid chromatography separates analytes as a function of time. Therefore, the data obtained from the LC portion is time-based, i.e., retention time $(R_t)$. Different analytes will elute from the solid phase element of the LC system (the column) at different times depending upon the eluant, etc. This differential separation allows for a $R_t$ characteristic for each analyte. This information can be useful in determining, for example, the identity of a particular analyte.

The second and third parameter is specific to the MS portion of the LC/MS system. Once a sample is separated via LC, individual analytes enter the MS portion of the system. Depending upon the conditions of the MS, the analyte will be ionized within a given volume and then be accelerated to a molecular mass detector. The mass-to-charge ratio (m/z) and intensity can be determined following mass detection. This information is used to determine differences between two or more samples.

Typically, PCA analysis is used to perform this determination using only the m/z and intensity parameters. Thus, the $R_t$ data does not contribute to the overall analysis. This tradeoff has been accepted because of the abundance of data available from the mass spectrometer, with approximately 5 to 10 AMU points per ion peak. The present invention addresses this failure by incorporating data binning. With data binning, the $R_t$ information is not lost in the PCA analysis, thus facilitating three-dimensional data analysis. Comparison between samples now includes $R_t$, m/z, and intensity data. This technique is especially useful in surveying the results of a complex sample, where the answer to a simple question must be found in masses of complex data. Hence, subtle changes between samples heretofore undetectable can now be elucidated.

In one embodiment, individual LC/MS chromatogrms are divided into predetermined fractions (or bins). These bins reflect the $R_t$ parameter. The size of the bin is determined by the operator. For example, the bin size can be one minute, reflecting one minute intervals along the chromatogram Within each bin, the intensity information for all the scans performed during the bin time are summed for each species (m/z )present during the corresponding $R_t$. The bin, or more precisely the data contained within it, is then transformed and exported to a data matrix such as a commercial spreadsheet, for example, Excel. Therefore, the original graphical data is transformed into a tabular form of data The information within each bin that is transformed are chromatographic time, m/z and intensity. More than one bin can undergo this transformation. For example, there can be sixty bins representing one bin per minute for a sixty minute LC procedure. Alternately, bins may be organized in an overlapping fashion so that for instance, ninety one-minute bins originating once per 40 seconds are used to analyze a sixty minute LC procedure. Once the transformation is complete, the data sets (data within the table) are aligned with zeros. Alignment of the data sets simply refers to a gap filling procedure, For example, if in bin 3 at m/z=100 there is an intensity value of 102 and in bin 4 at m/z100 there is no intensity value, then a zero is placed in bin 4 at the intensity position corresponding to m/z=100. In other words, the zero serves as a place holder, thus allowing for proper data alignment. Hence, each data set has one intensity value (including zero) for each m/z. Additionally, isotope abundance maybe combined, for example, combining values for $C^{12}$ and its isotope $C^{13}$. Finally, the spreadsheet files are transferred to a commercial PCA system, for example, Mat-Lab, for PCA analysis.

BRIEF DESCRIPTION OF THE DRAWINGS

FIG. 1 is a schematic showing the steps involved in an embodiment of the present invention;

DETAILED DESCRIPTION

Figure 2C:
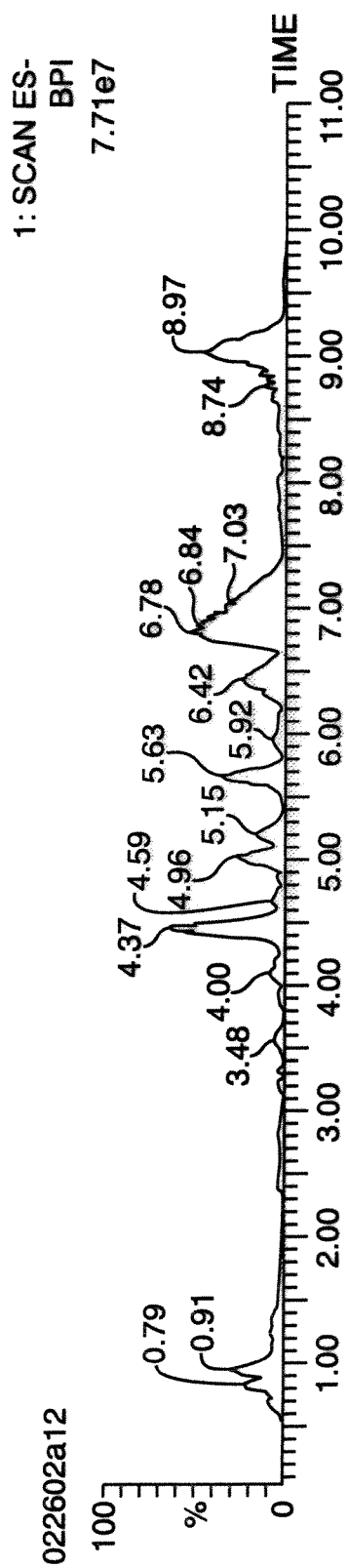
FIG. 2 is a comparison of negative ion BPI LC/MS chromatograms for control and dosed rats.

This invention pertains to a method of analyzing multi-dimensional data using a tool that handles fewer dimensions. This invention has particular applicability to analysis of the data from a chromatography procedure followed by a spectrometric procedure. The data set in these cases has a time component, as well as typically an intensity value for a physical or chemical characteristic of the sample. In a particular embodiment, this invention pertains to a method of analyzing data obtained from a Liquid Chromatography (LC)/Mass Spectrometry (MS) procedure using Principle Component Analysis (PCA). Typically, PCA analysis is performed using only two-dimensional data. In the present invention, the analysis is performed using three-dimensional data. The detailed description of the LC/MS and PCA analysis illustrates the methodology of the general case as well as this specific embodiment.

The chromatography portion of the system permits separation of analytes within a sample matrix. The information obtained from such a procedure is typically reported as retention time ($R_t$). As the analytes progress through the system, they enter the MS region of the LC/MS system. There they are ionized and a mass detector then detects these ionized species providing m/z and intensity information. Therefore, an LC/MS system can furnish at least three pieces of information. While many multi-variant statistical analysis techniques can be used, principle component analysis (PCA) is a robust method of analyzing data and is quite useful when making comparisons between different samples. However, PCA analysis is typically performed using only a two-dimensional data set. Therefore, it is expected that at least one parameter of data obtained from a LC/MS operation is lost. In the present invention, the analysis is performed using three-dimensional data sets along with PCA analysis.

A commonly employed method to separate analytes in a sample matrix is chromatography, in particular, liquid chromatography (LC) although gas chromatography (GC) provides similar data for sample that are gaseous. High Performance Liquid Chromatography (hereinafter "HPLC") allows for fast and efficient separation and characterization of analytes within a given sample. Components of an HPLC system include high pressure pumps which facilitate the movement of an aqueous and/or organic phase through the system. This aqueous phase (or mobile phase) comprises a solvent that is used to initially equilibrate the HPLC system. The solvent also provides an aqueous milieu for analytes to traverse through the entire HPLC system. Finally, the mobile phase comprises solvent which elutes analytes from an HPLC column.

Another component of an HPLC system is the chromatography separations column. The column comprises a solid phase. This solid phase, in combination with the mobile phase, effectuates differential separation of analytes contained within a sample matrix. The solid phase generally consists of chemical polymers that interact with a certain class of analytes. For example, a reverse-phase HPLC column has a solid phase chemistry (e.g., a hydrocarbon chain consisting of eighteen carbons attached to a silica bead) that interacts with analytes via hydrophobic forces.

Once the analytes are eluted from the column, they traverse into and through a detector. There are a variety of detection systems that can be employed in an HPLC system. For example, there are ultra-violet ("UV") detectors that detect analytes within the UV range, infrared (IR) detectors that detect analytes within the IR range, electro-chemical detectors that detect analytes using voltametric techniques, nuclear magnetic resonance detectors that detect analytes based on their response to a magnetic field, and mass spectrometer detectors that detect analytes based on the mass to charge ratio.

In an LC/MS system, the sample matrix is first subjected to LC separation, thereby effectuating the separation of analytes within the sample. This information, often conveyed by an analyte's $R_t$, can be used for characterizing and identifying the analyte. However, further information can be obtained, especially for comparisons made between different samples, by subjecting the analytes to MS detection. In general, mass spectrometers ionize molecules within a given volume and then accelerate the ionized molecules to a molecular mass detector. Ionization of a molecule can occur through electron-ionization, chemical ionization, electrospray ionization, or photoionization. The ionization process can occur under various pressure conditions, including atmospheric pressure. Information obtained from MS includes the intensity of response for a particular m/z value. It is this intensity (as well as m/z) information that is important when comparing two or more samples.

The MS information can be harnessed for comparative analysis. For example, assume that one is experimenting with a human cell line. The goal of the study is to determine what if any effect compound X has on a particular metabolite. To continue, assume that the operator has obtained two samples, sample 1, a control sample, i.e., cell extract from a cell culture in which no compound X was added, and sample 2, a cell extract taken from a cell culture system in which compound X was added. These two samples can be subjected to LC/MS. Let us further assume that the metabolite of interest is amenable to chromatographic isolation using a reverse-phase column. Once separated via LC, the samples, sample 1 and sample 2 independently, can be subjected to MS analysis. The MS signals generated from the two samples can then be compared, particularly for the metabolite of interest to determine if its intensity increases, decreases, or remains unaffected by the addition of compound X.

FIG. 1 shows a flow chart depicting the various steps of the present invention as applied to a LC/MS experiment. FIG. 1a depicts in a graphical format data obtained from an LC/MS procedure on a fictitious sample. As shown, the graph defines three parameters. The X-axis defines the m/z parameter, for example, the X-axis can extend from 100 to 800 m/z in 0.1 m/z steps. The Y-axis of FIG. 1a represents the intensity or response parameter. The intensity can be set as a percentage of a certain ion, e.g., the base peak. Finally, there is a Z-axis that represents the time parameter. Depicted in FIG. 1a are ion species differing in at least one if not all three parameters. Yet each ion species is uniquely defined by the parameters in FIG. 1a Extant PCA analysis requires that the data represented in FIG. 1a be converted into a two-dimensional data set prior to analysis. For example, conventional PCA analysis can be performed using the m/z and intensity parameters. However, this would eliminate the time parameter. A more thorough analysis would include all relevant information available including the time dimension. FIG. 1b represents a process whereby all three parameters can be conserved and subjected to analysis. Data binning is a process of separating one data set representing multiple measurement points into multiple data sets that aggregate measurement points. A bin corresponds to a range of one parameter, the bin parameter. The variation of the bin parameter within each bin is eliminated such as by accumulating all data points within the bin at the bin value. Note that a bin that encompassed the entire data set has the same effect as ignoring the bin parameter. While it is most common to utilize disjoint bins, overlapping bins may be used for some analysis. In transitioning from FIG. 1a to FIG. 1b, a process of data binning occurs wherein a predetermined bin size is selected. The bin size is a function of the time dimension. For example, the bin size can be two minutes. Multiple bins are shown in FIG. 1b. Each bin contains both m/z and intensity information for ion species found in all the scans falling within that bin. The bin (or region) sizes are selected by a practitioner based on experience and the sample being tested. Selection methods are well known to those skilled in the art. For example, MassLynx software can be employed. Using this software, a bin is collected as follows: (1) open the total ion chromatogram; (2) select a bin region by right mousing and dragging over the bin area, a combined mass spectrum will appear (the bin); (3) in the combined mass spectrum (bin) window, a "List Spectrum" option will appear and is activated; (4) as List Spectrum is chosen, a window displays m/z with its corresponding abundances in a two column format; (5) copy the data contained within the two columns; and (6) paste into a spreadsheet like Excel.

Following the data binning process, a transformation step occurs. (See FIG. 1b to FIG. 1c). This transformation converts the separate lists derived from the graphical data format into a matrix data representation. A practitioner can begin this transformation by simply employing a "cut and paste" procedure, delivering the two column data set information to a commercial spreadsheet like Excel. Once this part of the transformation is complete, the data set needs to be aligned with zeros. Each bin must have a value of all the ions to be analyzed. In order to assure analysis fidelity, zeros are inserted as intensity values where no ion signal was observed for that bin, resulting in each data set having one intensity value for each m/z parameter. Then the m/z parameter columns can be melded into one column that acts as one axis of the matrix. Alternatively, a software program can be used to automate this transformation. A depiction of the tabular representation is shown in FIG. 1c. In FIG. 1c there is a m/z column and a bin row. The m/z column contains the m/z ions to be analyzed. The bin row contains the desired bins to be analyzed. The matrix intersection contains intensity values corresponding to proper m/z and bin parameters. Further data manipulation, based on known transformations in m/z and intensity caused by the test, may be done by the operator before the data is subjected to analysis. For instance, isotope abundance can be combined so that the values for, for instance, $C^{12}$ and its isotope $C^{13}$ are combined.

The matrix or spreadsheet is then transferred and subjected to a commercial PCA program where comparisons between various samples can be performed. One such commercial PCA program is MatLab available from MathWorks, Natick, Mass. Another PCA package can be obtained from InfoMetrix, located in Woodinville, Wash., and is called Pirouette.

By blurring some of the mass spectrometer's inherent high resolution by combining the data resulting from multiple scans via binning, the two-dimensional analysis can handle the resulting three dimensional data is allows the mass of data to be analyzed where a change between specimens is expected but the location of the change in the various scans is not known. After the location of the variation is known, later analysis can used the high resolution inherent in the raw data to further characterize the differences. The binning technique can be applied to adapt data sets to many types of multi-variant statistical analysis.

The features and other details of the invention will now be more particularly described and pointed out in the following example. It will be understood that the particular embodiments of the invention are shown by way of illustration and not as limitations of the invention. The principle features of this invention can be employed in various embodiments without departing from the spirit and scope of the invention.

EXAMPLE

Rat Urine Samples:

A total of 20 rat samples were used for this experiment. The rats were divided into four (4) groups. Group I received the dosing matrix alone, Group II, III, and IV were orally dosed with compounds A, B, and C, respectively. Samples of rat urine were collected at two time points, 0-8 and 8-24 hours after dosing. The rat urine was stored frozen at $-20°$ C. prior to analysis.

Chromatography:

The chromatography was performed using a Waters Alliance 2795 HT equipped with a column oven and a Waters 2996 PDA detector. A 20 µL/min injection of rat urine (diluted 1:4 with distilled water) was made onto a 10 cm×2.1 mm Waters Symmetry $C_{18}$ 3.5 µm column. The column was maintained at 40° C. and eluted under gradient conditions at a flow rate of 600 µL/min, where eluant "A" was 0.1% aqueous formic acid, and eluant "B" was acetonitrile. The column was maintained at 100% A for the first minute, then the mobile phase was rapidly increased to 30% B over the next 7 minutes. The mobile phase was then rapidly increased to 95% B over 0.1 minutes. This mobile phase was maintained for 0.5 minutes in order to wash the column and then returned to the initial conditions over 0.1 minutes. The next injection was made 10 minutes after the first injection.

Mass Spectrometry

The mass spectrometric analysis was performed on a MicroMass Quattro Micro equipped with an electrospray interface ("ESI"). The instrument was operated in negative ion mode with a capillary voltage of 3 kV, the cone voltage was set to 25 Volts, the nebulizer gas was set at 600 L/hr with a desolvation temperature of 150° C. and a source temperature of 70° C. The column effluent was split in a ratio of 5:1, such that 100 µL/min entered the mass spectrometer source. The instrument was operated in full scan mode, scanning from 100-800 m/z with a scan time of 200 msec and an interscan delay time of 50 msec. Data was collected from 0-10 minutes. The initial portion of the chromatogram was not directed to waste.

Data Analysis:

The LC/MS chromatograms were inspected for the presence of any drug-related products such as Phase I and Phase II metabolites. Each individual LC/MS chromatogram was then divided into 10 fractions of 100 scans. The MS signal was combined for each individual chromatogram fraction of 100 scans. The peaklist and ion abundances were then exported to an Excel file. The data sets were then aligned with zeros being inserted as intensity values where no ion signal was observed, such that each data set had one intensity value for each m/z integer between 100 and 800. The Excel files were then transferred to MatLab for PCA analysis using an in house program.

Discussion:

Rat urine potentially contains several thousand components most of which remain unknown. The vast majority of these components are of moderate or high polarity, hence, it was only necessary to employ a gradient from 0-30% organic content to effect complete elution of all of the components in the urine samples. Negative ion ESI MS was chosen as the mode of MS detection as it gave a more information rich data set than positive ion ESI. The chromatography column length, gradient time, and effluent flow rate employed in this study was chosen to give the best balance between sample throughput and chromatographic resolution. It provided a sample throughput of 6 samples per hour and a peak capacity of 78.

While this peak capacity is not very high, the use of mass spectrometry scanning from 100-800 m/z provides a much greater effective peak capacity. In this study, we have employed a simple reverse-phase chromatography system. It is fully appreciated that many highly polar compounds, such as amino acids and sugars, will not be retained. Modifying the system permits elucidation of these compounds.

Figure 2D:
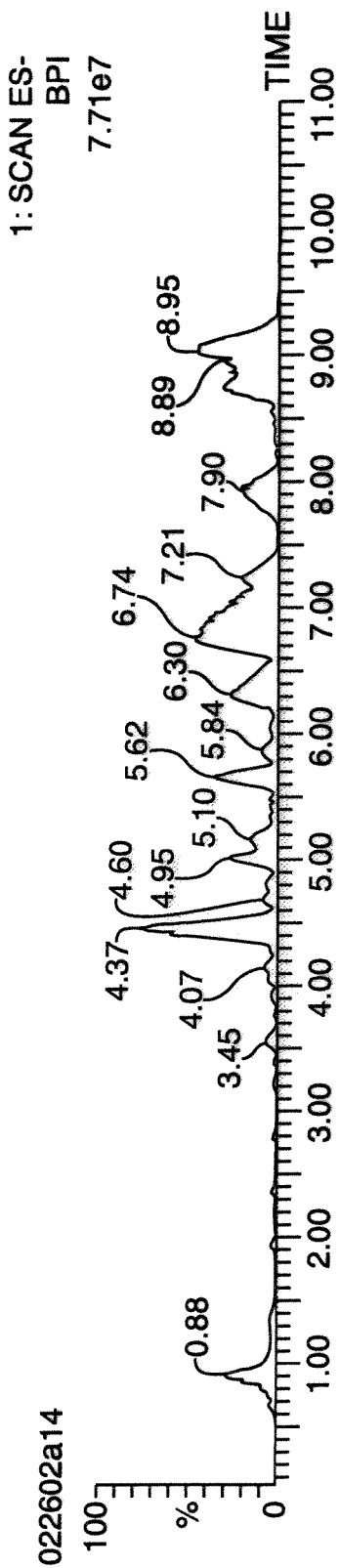

A preliminary comparison of the base peak intensity ("BPI") chromatograms of the control rat urine and urine samples from the dosed animals at time point 1 reveals a qualitative difference, see FIG. 2. As can be observed from these chromatograms, there are several peaks in the dosed sample group chromatograms that show elevated levels when compared to those in the control group. These peaks elute in the 5-9 minutes time region of the chromatogram. A thorough investigation of these peaks confirmed that none of them were metabolites resulting from the dosed compounds. Therefore, these peaks must be due to a change in the metabolic state of the animals.

Figure 3A:
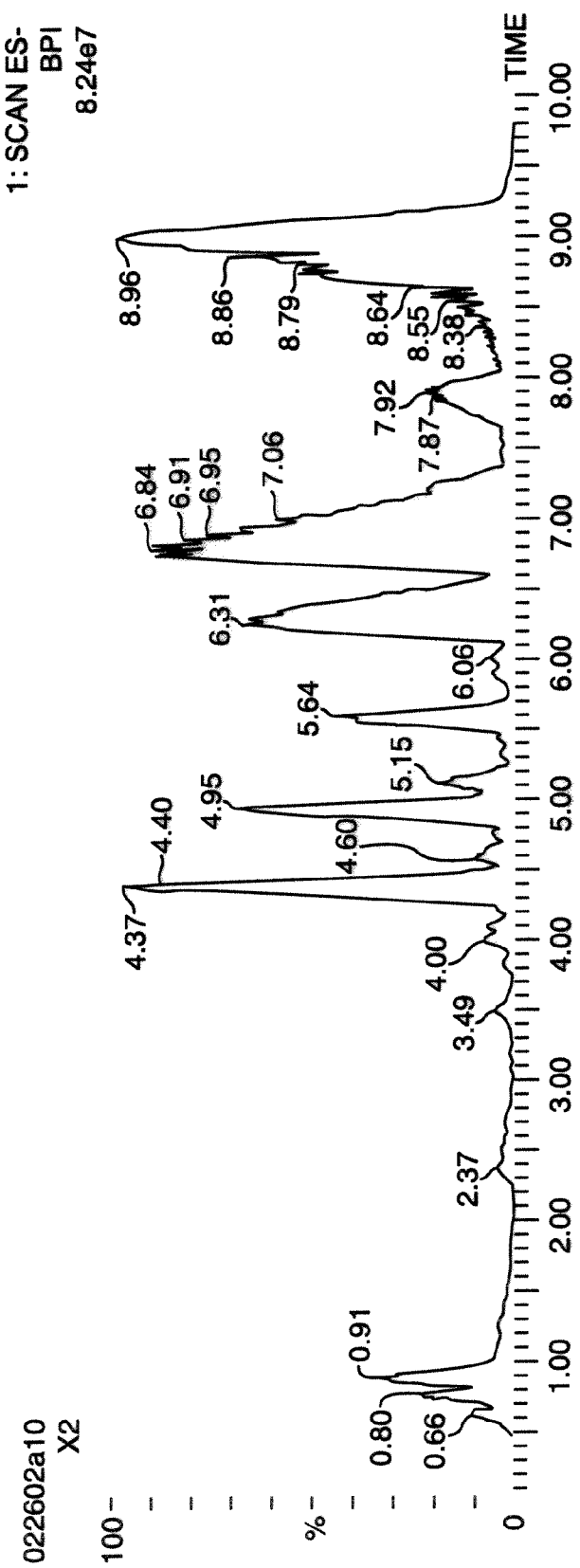
FIG. 3 is a comparison of negative ion BPI LC/MS urine chromatograms from rats dosed with compound A at time point 1 and time point 2.
Figure 3B:
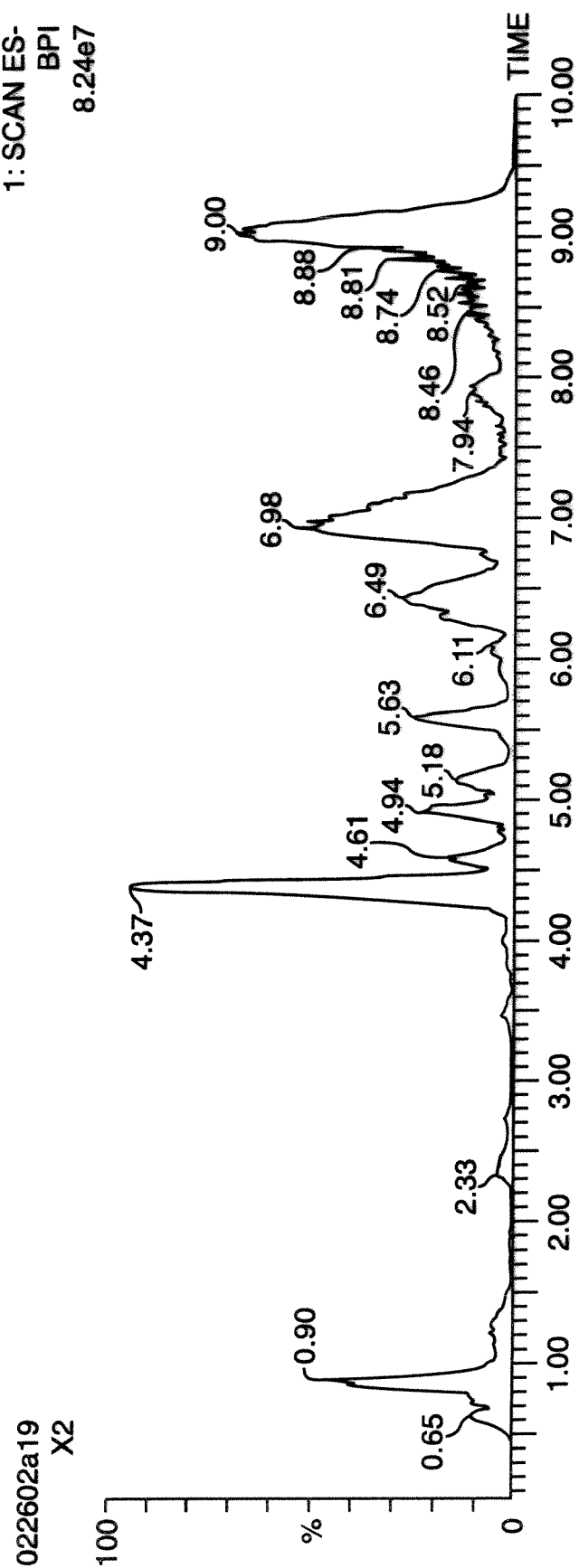
Figure 4A:
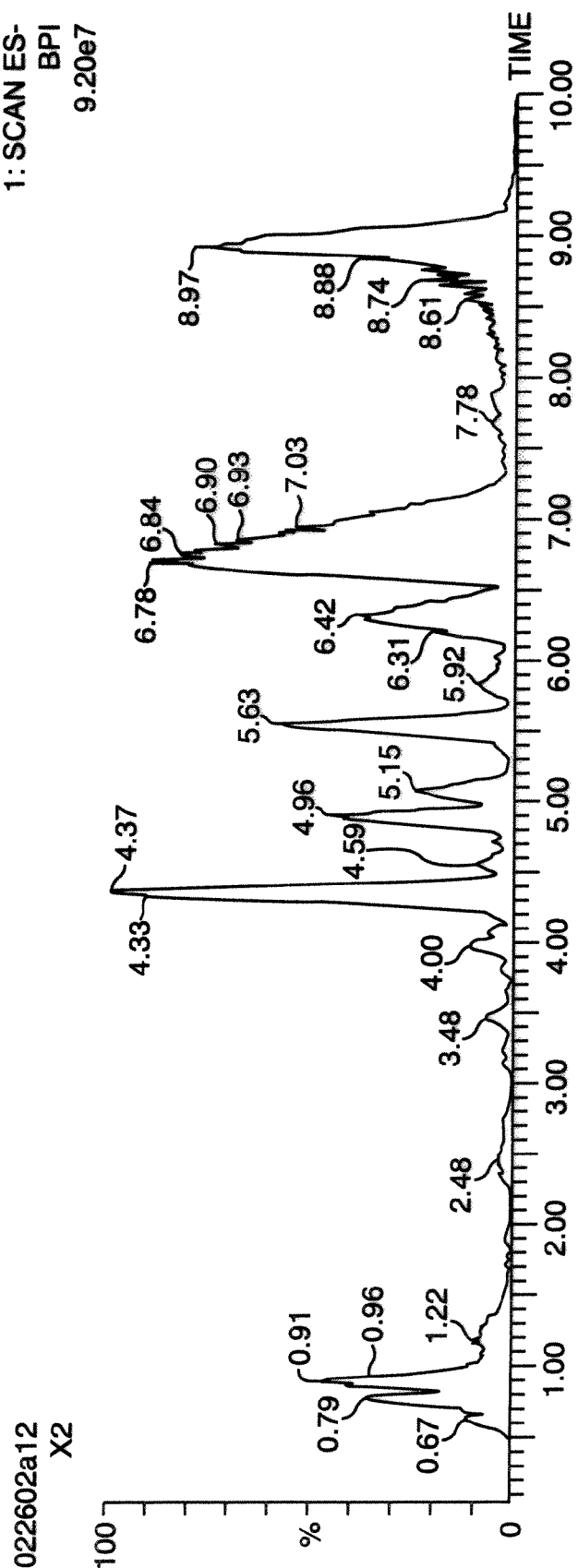
FIG. 4 is a comparison of negative ion BPI LC/MS urine chromatograms from rats dosed with compound B at time point 1 and time point 2.
Figure 4B:
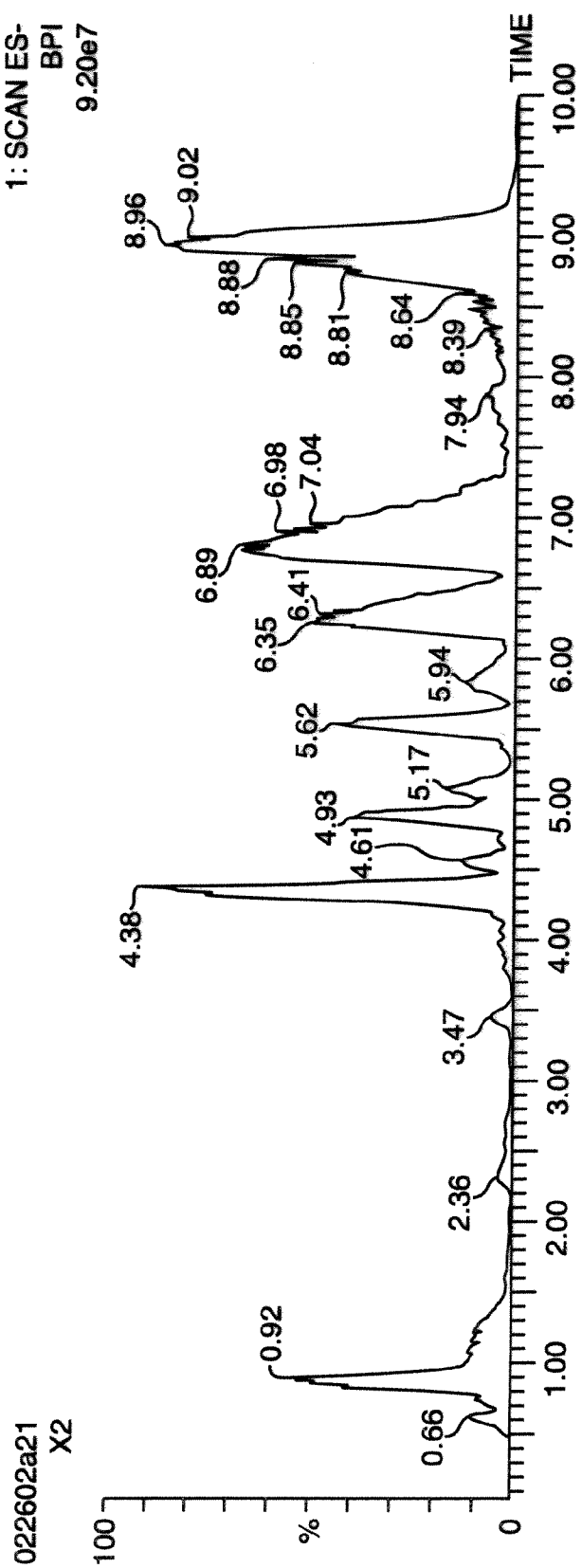
Figure 5A:
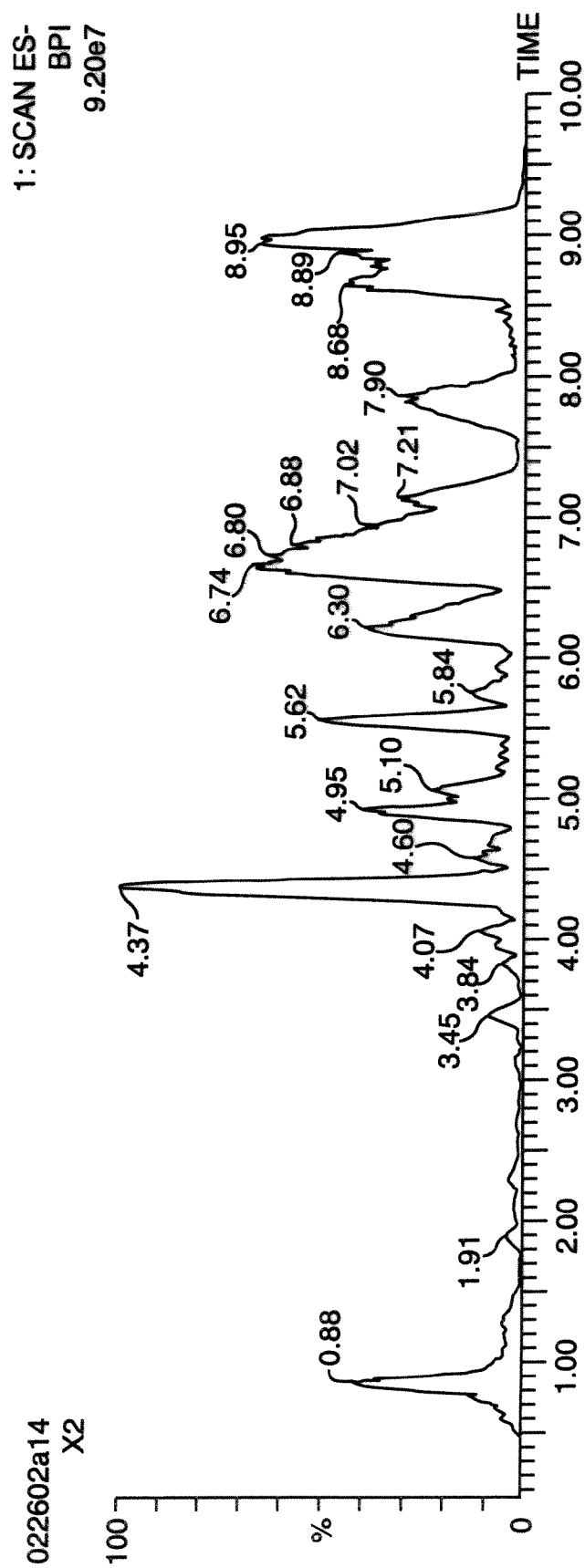
FIG. 5 is a comparison of negative ion BPI LC/MS urine chromatograms from rats dosed with compound C at time point 1 and time point 2.
Figure 5B:
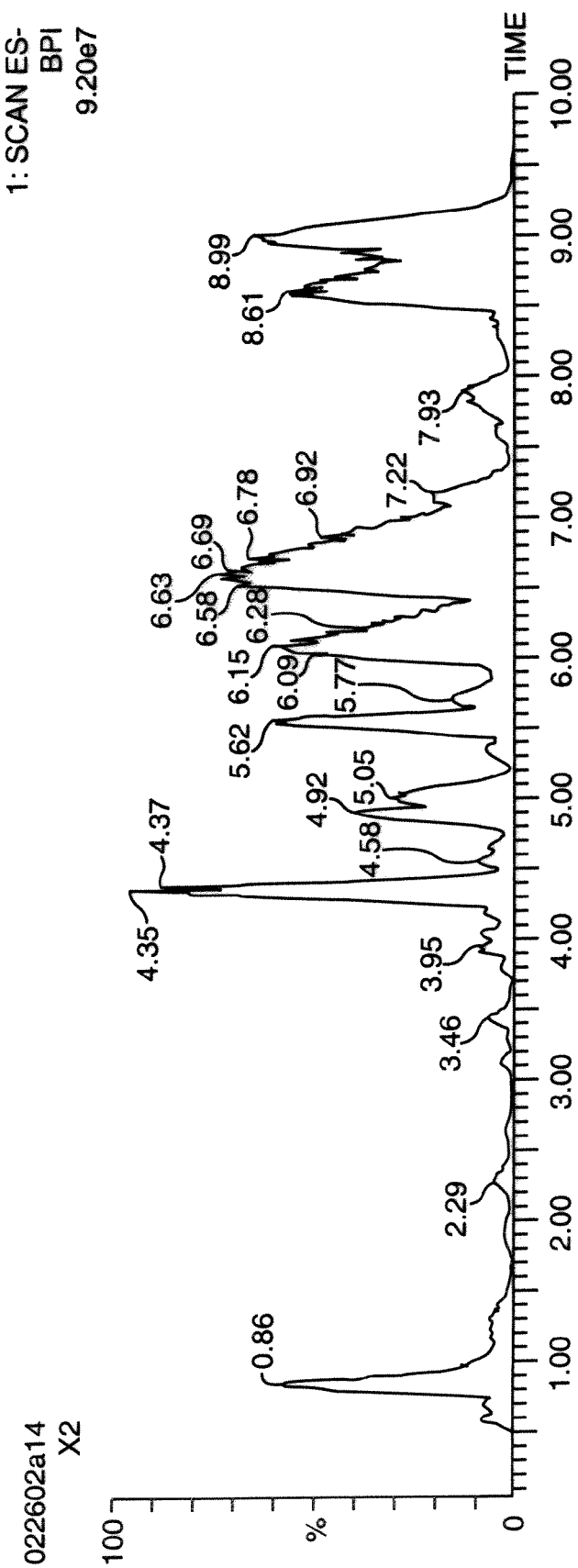

The BPI chromatograms obtained from the time point 2 samples for compound "A" shows some subtle changes in some peak intensities when compared to the time point 1 samples, see FIG. 3. In the time point 2 sample, the analytes eluting between 5-7 minutes seems to have reduced relative concentration compared to those same analytes in time point 1. The samples for compounds "B" and "C" show less variation between time points 1 and 2, see FIGS. 4 and 5. As these time point 1 and 2 samples are day and night samples one would expect to see a significant variation between the two sample types even without the dosing of a xenobiotic. This implies that the compounds associated with the changes in animal metabolism between day and might were either not retained or not detected.

Figure 6A:
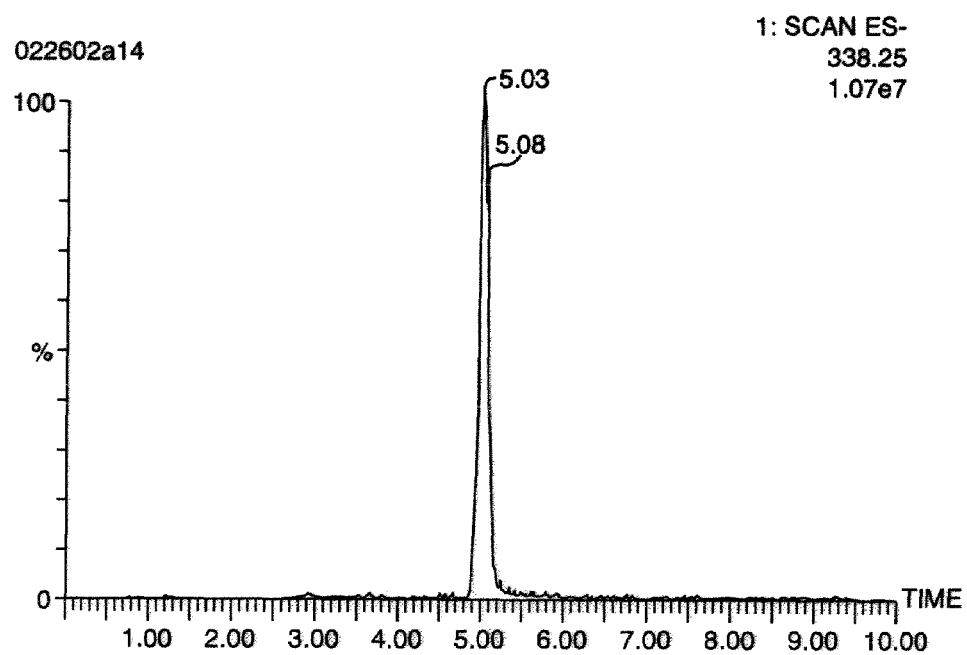
FIG. 6(*a*) is an extracted ion chromatogram, and (*b*) is an MS spectrum for peaks 338 m/z.
Figure 6B:
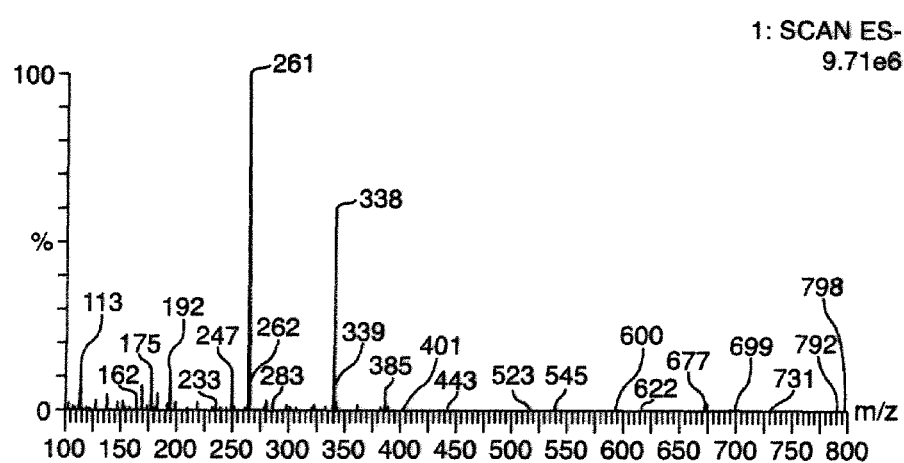

The peaks identified to have changed in the dosed samples compared to the control are listed in Table 1. (An extracted ion chromatogram of one of these ions at m/z=338 and the MS spectrum of this peak are given in FIG. 6.)

TABLE 1

| Compound dosed | Analyte m/z value | Relative change |
| --- | --- | --- |
| A | 283 | 10 fold increase |

TABLE 1-continued

| Compound dosed | Analyte m/z value | Relative change |
|---|---|---|
| A | 461 | 5 fold increase |
| A | 187 | 10 fold increase |
| B | 338 | 2 fold decrease |
| B | 283 | 10 fold increase |
| B | 461 | 10 fold increase |
| B | 187 | 10 fold increase |
| C | 283 | 20 fold increase |
| C | 187 | 30 fold increase |

The data in Table 1 illustrate the changes in peak intensity observed for these peaks in the control samples and the dosed samples. As can be observed from this data, the changes in the peak concentrations are very significant. The fact that these compounds were also observed in the control samples confirms that these peaks were not metabolic products of the dosed compounds.

Figure 7:
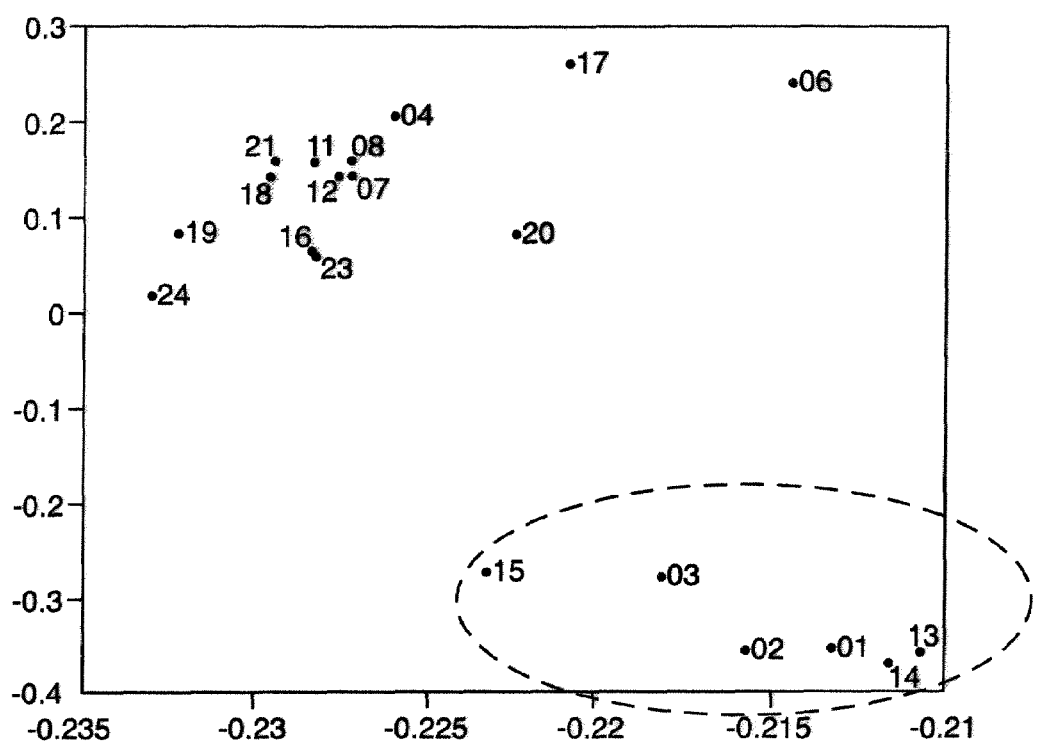
FIG. 7 is a PCA plot of an ere data set consisting of rat urine samples 1-24.

The PCA analysis of the entire data set is presented in FIG. 7. In this figure, the data relating to the control samples are contained within the ringed areas. The control samples are clearly separated from the dosed animal samples. This PCA analysis was performed using the entire data set of retention time and m/z values. Fractionating the chromatogram into 10 time regions also allowed PCA analysis to be performed on specific time regions of the chromatogram.

Figure 8A:
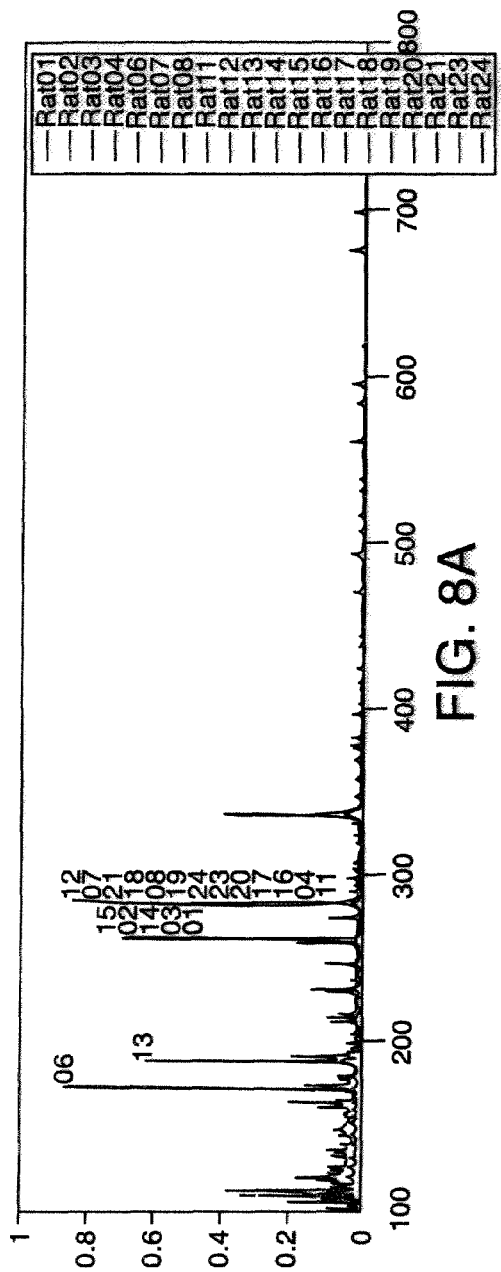
FIG. 8(*a*) is a combined and overlaid mass spectra, and (*b*) is a PCA plot of fraction from 5 minutes to 6 minutes.
Figure 8B:
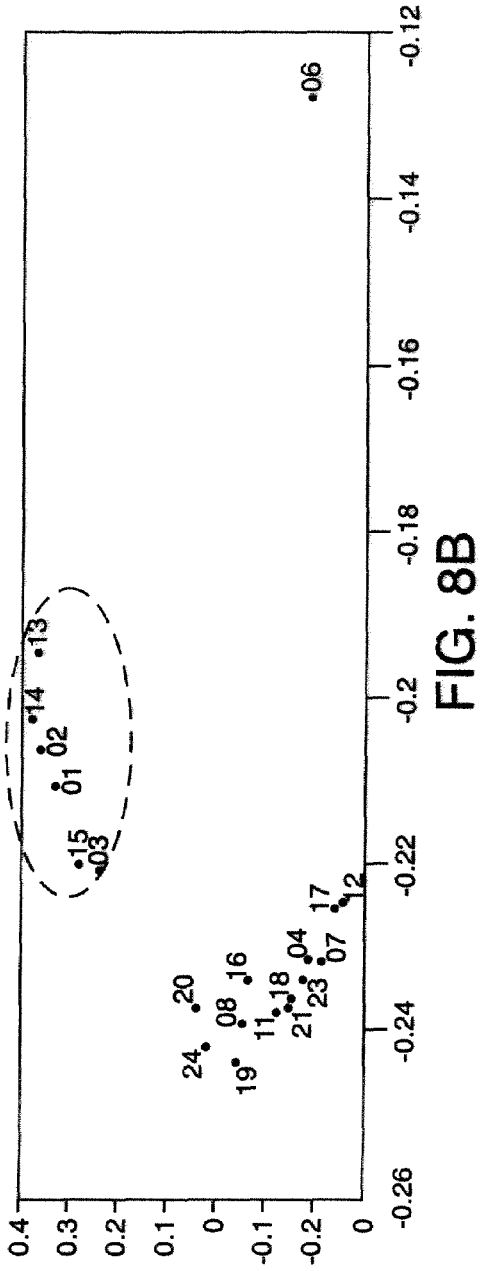
Figure 9A:
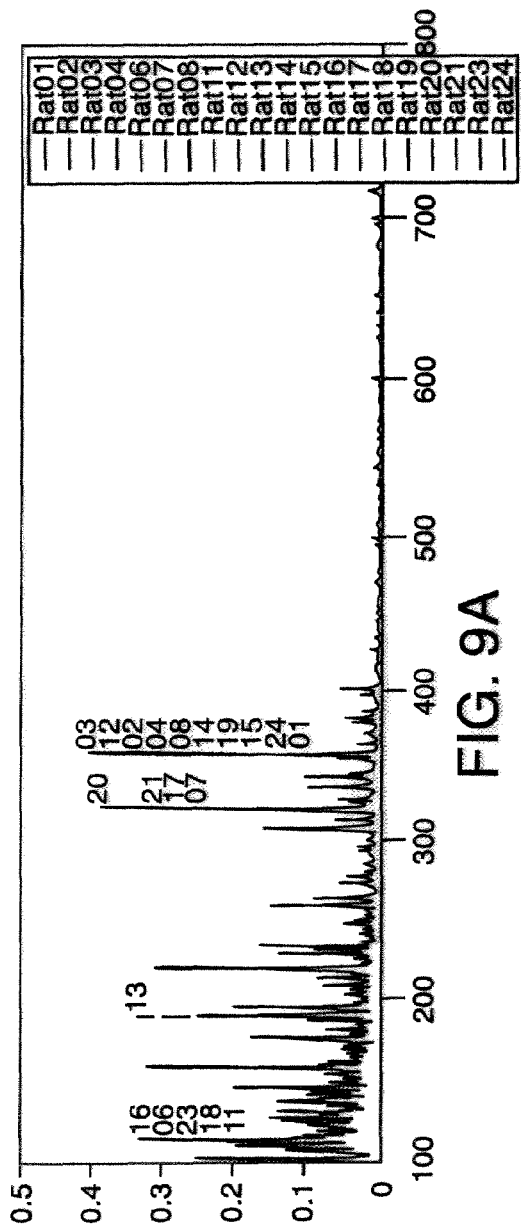
FIG. 9(*a*) is a combined and overlaid mass spectra, and (*b*) a PCA plot of fraction from 3 minutes to 4 minutes.
Figure 9B:
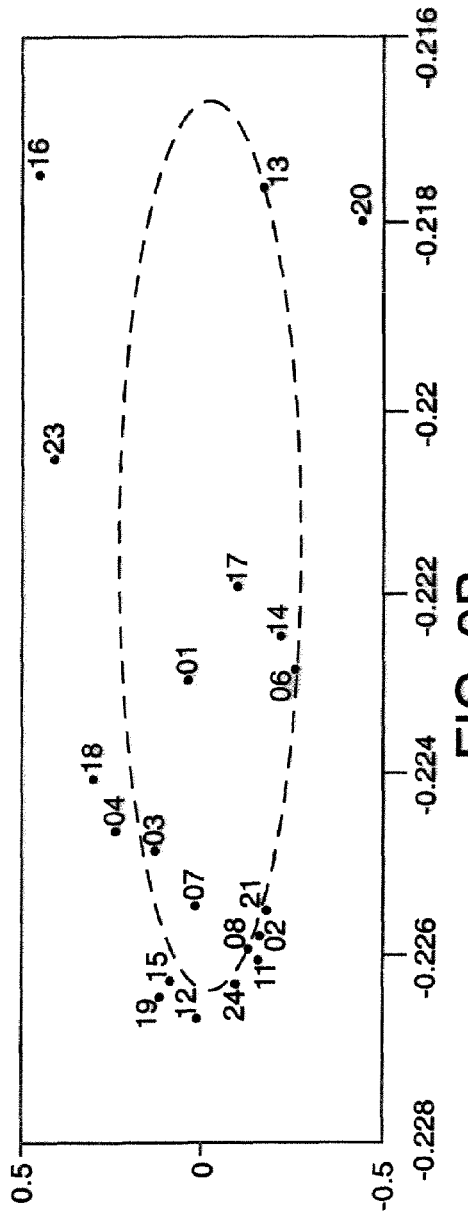

The PCA analysis of the data between 5 and 6 minutes is presented in FIG. 8. Here it is possible to separate the control samples, contained inside the ringed area, from the dosed samples. The combined MS spectrum indicates that the MS peaks responsible for the mapping of the dosed and control samples to different regions of the PCA plot were m/z=283 and m/z=261. The m/z=283 ion has increased in intensity in the dosed samples whereas the m/z=261 ion has reduced in intensity in the dosed samples. This result confirms the observations made by analyzing the LC/MS data FIG. 9 shows the PCA analysis of the LC/MS data between 3 and 4 minutes. In this data, there is no separation between the control and dosed samples. This data indicates that in the region of the chromatogram there was no significant difference between the dosed and control samples.

The application of LC/MS coupled to PCA data analysis has been successfully applied to the screening of rat urine following the administration of three candidate pharmaceuticals. With this methodology, it was possible to differentiate the control samples from the dosed samples. It was also possible, using PCA analysis, to identify the components of the MS spectrum responsible for the separation. This data clearly demonstrates that LC/MS is a viable alternative or even complementary to proton NMR for metabonomic applications in drug discovery and development.

While this invention has been particularly shown and described with reference to embodiments thereof, it will be appreciated by those skilled in the art that various changes in form and detail may be made therein without departing from the spirit and scope of the invention as defined by the appended claims hereto.

What is claimed is:

1. A method of analyzing three-dimensional data derived from at least two samples using a two-dimensional analysis technique, comprising:
(a) obtaining data for said samples, said data characterized by at least a first parameter, a second parameter, and a third parameter, at least the third parameter being correlated with time;
(b) binning said obtained data to form a plurality of binned data sets for each of said samples, wherein a bin size is selected based on the third parameter correlated with time and data points of each binned data set are characterized utilizing the first and second parameters;
c) inserting null values of the second parameter to transform said binned data sets into aligned binned data sets;
(d) for each of said samples, a two-dimensional array from said aligned binned data sets by associating said first parameter with one axis of the two-dimensional array and associating bin numbers with a second axis of the two-dimensional array, wherein values of said second parameter of the data points of said binned data sets are associated with elements of the two-dimensional array;
(e) subjecting each of said two-dimensional arrays to a two dimensional multi-variant statistical analysis; and
(f) determining a time bin associated with a difference in a level of at least one component, between at least two of said samples, by comparing data associated with said analyzed two-dimensional arrays.

2. The method of claim 1 wherein said two dimensional multi-variant statistical analysis is chosen from the set consisting of classical least squares analysis (CSL), principle component analysis (PCA), partial least squares analysis (PLS) and partial least squares discriminant analysis (PLS-DA).

3. The method of claim 2 wherein said two-dimensional multi-variant statistical analysis is principle component analysis (PCA).

4. The method of claim 1 wherein said three-dimensional data is derived from a chromatographic process combined with a spectrometric process.

5. The method of claim 4 wherein said chromatographic process is a liquid chromatography process.

6. The method of claim 4 wherein said spectrometric process is chosen from the set consisting of ultraviolet spectroscopy, infrared spectroscopy, mass spectrometry and nuclear magnetic resonance.

7. The method of claim 6 wherein said spectrometric process is mass spectrometry.

8. The method of claim 4 wherein the first parameter is a physically accessible variable corresponding to a physical/chemical property of said sample and the second parameter is an intensity of said variable and said third parameter correlated with time is a duration of $R_t$.

9. The method of claim 8 wherein said physically accessible variable corresponding to a physical/chemical property of said sample is m/z.

10. The method of claim 4 wherein said three-dimensional data is derived from a liquid-chromatography/mass spectrometry process.

11. A method of analyzing three-dimensional data using principle component analysis (PCA), comprising:
(a) obtaining chromatography/mass spectrometry data for a sample, said data characterized by at least three parameters including $R_t$, m/z and intensity;
(b) binning said obtained data to form a plurality of binned data sets, wherein a bin size is selected based on $R_t$ and data points of each binned data set are characterized using one or more values of the m/z and intensity parameters for each of one or more ion species associated with each bin;
c) inserting null values of the intensity parameter to transform said binned data sets into aligned binned data sets;
(d) forming a two dimensional array from said aligned binned data sets by associating said m/z parameter with one axis of the two dimensional array and associating bin numbers with a second axis of the two dimensional array, wherein values of the intensity parameter of the data points of said binned data sets are associated with elements of the two-dimensional array;

(e) subjecting said two dimensional array to PCA analysis; and (f) determining a time bin associated with a change in the sample relative to a second sample.

12. The method of claim 11 wherein said chromatography/mass spectrometry data is derived from a liquid-chromatography/mass spectrometry process.

* * * * *